US012633382B2

(12) United States Patent
Neil et al.

(10) Patent No.: US 12,633,382 B2
(45) Date of Patent: May 19, 2026

(54) RANKING BIOLOGICAL ENTITY PAIRS BY EVIDENCE LEVEL

(71) Applicant: BENEVOLENTAI TECHNOLOGY LIMITED, London (GB)

(72) Inventors: Daniel Lawrence Neil, Williamsburg, VA (US); Alix Mary Benedicte LaCoste, Brooklyn, NY (US); Alexander DeGiorgio, London (GB); Ian Churcher, Cambridgeshire (GB); Russell David Sutherland, London (GB); Yingkai Gao, Brooklyn, NY (US)

(73) Assignee: BENEVOLENTAI TECHNOLOGY LIMITED, London (GB)

( * ) Notice: Subject to any disclaimer, the term of this patent is extended or adjusted under 35 U.S.C. 154(b) by 537 days.

(21) Appl. No.: 17/625,113

(22) PCT Filed: Jul. 10, 2020

(86) PCT No.: PCT/GB2020/051667
§ 371 (c)(1),
(2) Date: Jan. 6, 2022

(87) PCT Pub. No.: WO2021/009493
PCT Pub. Date: Jan. 21, 2021

(65) Prior Publication Data
US 2022/0270718 A1 Aug. 25, 2022

Related U.S. Application Data

(60) Provisional application No. 62/874,235, filed on Jul. 15, 2019.

(51) Int. Cl.
*G16H 50/70* (2018.01)
*G06N 3/02* (2006.01)
(Continued)

(52) U.S. Cl.
CPC ............... *G16H 10/20* (2018.01); *G06N 3/02* (2013.01); *G06N 5/025* (2013.01); *G16H 50/70* (2018.01)

(58) Field of Classification Search
CPC .......... G16H 10/20; G16H 50/70; G06N 3/02; G06N 5/025
See application file for complete search history.

(56) References Cited

U.S. PATENT DOCUMENTS

2005/0060305 A1 3/2005 Hopkins et al.
2007/0005344 A1* 1/2007 Sandor .................. G06F 16/313
707/E17.084
(Continued)

OTHER PUBLICATIONS

Xin Yang, Yifei Wang, Ryan Byrne, Gisbert Schneider, and Shengyong Yang Chemical Reviews 2019 119 (18), 10520-10594 DOI: 10.1021/acs.chemrev.8b00728 (Year: 2019).*
(Continued)

*Primary Examiner* — Matthew L Hamilton
(74) *Attorney, Agent, or Firm* — Smith Baluch LLP

(57) ABSTRACT

A computer-implemented method of electronically mining medical and scientific datasets to determine a ranking indicating a level of evidence for an association between two entities is disclosed. The method comprises receiving a representation of an entity pair, performing first data mining on one or more unstructured datasets to generate one or more first scores each representing an extent of association between the entities of the entity pair, and performing second data mining on one or more structured datasets to generate one or more second scores each representing an extent of association between the entities of the entity pair. The method also comprises using a classifier to determine a predicted ranking for the entity pair using the one or more first scores and the one or more second scores, and providing (Continued)

the predicted ranking to a user as an indication of the strength of evidence for an association between the entities of the entity pair.

24 Claims, 9 Drawing Sheets

(51) Int. Cl.
    *G06N 5/025*       (2023.01)
    *G16H 10/20*      (2018.01)

(56)                References Cited

U.S. PATENT DOCUMENTS

| | | | |
|---|---|---|---|
| 2013/0339005 A1* | 12/2013 | Zhang | G16B 40/20 |
| | | | 704/9 |
| 2017/0098032 A1 | 4/2017 | Desai et al. | |
| 2018/0032678 A1* | 2/2018 | Dandala | G16H 50/70 |
| 2019/0303535 A1* | 10/2019 | Fokoue-Nkoutche | |
| | | | G06F 17/16 |
| 2019/0304575 A1* | 10/2019 | Beltre | G16H 40/20 |
| 2020/0090818 A1* | 3/2020 | Tripathi | G16H 70/40 |
| 2020/0343000 A1* | 10/2020 | Kartoun | G16H 40/20 |
| 2021/0004586 A1* | 1/2021 | Akhondi | G06F 16/93 |
| 2021/0049442 A1* | 2/2021 | Menon | G06N 3/04 |

OTHER PUBLICATIONS

PCT Written Opinion and Search Report issued in connection with related PCT/GB2020/051667 date of mailing Oct. 14, 2020.

* cited by examiner

*200*

Receive entity pair ~*202*

Perform first data mining ~*204*

Generate first scores ~*206*

Perform second data mining ~*208*

Generate second scores ~*210*

Use classifier to determine ranking ~*212*

Provide ranking ~*214*

*400*

| Ranking | Criteria —402 | |
|---------|------|---|
| 1 | • ClinicalTrialData = Phase2success AND (AUS > 0.5 OR OpenTarget > 0.7) | |
| 2 | OR | • ClinicalTrialData in ReducedToPractice  AND AUS >0.2 <br><br> • SLPs ≥ 200 AND SLPp ≥ 100 <br><br> • AUS ≥ 0.35 <br><br> • OpenTarget = 1 |
| 3 | OR | • ClinicalTrialData is not NULL <br><br> • SLPs ≥ 6 AND SLPp ≥ 1 <br><br> • AUS ≥ 0.05 <br><br> • 0 < OpenTarget < 1 |
| 4 | Otherwise | |

*600*

Input first scores ~*602*

Input second scores ~*604*

Use classifier to determine ranking ~*606*

Determine loss ~*608*

Adjust threshold values ~*610*

RANKING BIOLOGICAL ENTITY PAIRS BY EVIDENCE LEVEL

CROSS-REFERENCE TO RELATED PATENT APPLICATIONS

This patent application is the 35 U.S.C. 371 national stage of International Patent Application PCT/GB2020/051667 filed 10 Jul. 2020, which claims the benefit of and priority to U.S. Application 62/874,235 filed 15 Jul. 2019, which is incorporated by reference herein for all purposes to the extent permitted by law.

The present application relates to a system and method for ranking biological entity pairs according to a level of evidence for an association between the entities of the pair. In particular, the determination of the ranking is based on data mining of medical and scientific datasets and may be optimised by various techniques.

BACKGROUND

When trying to identify new avenues for research from the available literature, drug discovery scientists need to analyse data from the literature and evaluate potential new treatment hypotheses. The goal is to find new but also viable avenues for research and, as such, associations between biological entities that have some support but not strong support from the literature are of interest. Pairs of biological entities are required that have an intermediate level of support for being associated with each other from the literature so that they can be prioritised for further research with a reasonable likelihood of resulting in new discoveries. Consequently, there is a need to automatically mine medical and scientific datasets to determine levels of evidence for associations between biological entities so that pairs of entities with middling levels of evidence can be more easily identified for further investigation.

The embodiments described below are not limited to implementations which solve any or all of the disadvantages of the known approaches described above.

SUMMARY

This Summary is provided to introduce a selection of concepts in a simplified form that are further described below in the Detailed Description. This Summary is not intended to identify key features or essential features of the claimed subject matter, nor is it intended to be used to determine the scope of the claimed subject matter.

In a first aspect, the present disclosure provides a computer-implemented method of electronically mining medical and scientific datasets to determine a ranking indicating a level of evidence for an association between two entities, the method comprising: receiving a representation of an entity pair; performing first data mining on one or more unstructured datasets to generate one or more first scores each representing an extent of association between the entities of the entity pair; performing second data mining on one or more structured datasets to generate one or more second scores each representing an extent of association between the entities of the entity pair; using a classifier to determine a predicted ranking for the entity pair using the one or more first scores and the one or more second scores; and providing the predicted ranking to a user as an indication of the strength of evidence for an association between the entities of the entity pair.

Optionally, each entity of the entity pair comprises a biological entity. Optionally, each entity of the entity pair comprises a drug, a compound, a disease, a biological mechanism, a biological pathway, a gene, another nucleic acid, a cell type, a tissue type, or a protein. Optionally, each of the one or more first scores is based on a respective one of the one or more unstructured datasets and/or each of the one or more second scores is based on a respective one of the one or more structured datasets. Optionally, the one or more first scores comprises at least one of an SLP score and an AUS score. Optionally, the one or more second scores comprise at least one of a phase II clinical trial success rating or a phase IV drug or genetic association score for the entity pair. Optionally, the classifier comprises a set of rules. Optionally, the set of rules comprises a threshold value for one or more of the first and second scores for determining the predicted ranking. Optionally, the threshold value is optimised using manually ranked entity pairs. Optionally, the threshold value is optimised using a statistical optimisation method or a machine learning algorithm. Optionally, the classifier comprises a model. Optionally, the model comprises a machine learning algorithm. Optionally, the machine learning algorithm comprises a neural network. Optionally, the model is trained using manually ranked entity pairs.

In a second aspect, the present disclosure provides a computer-implemented method of evaluating a database with respect to medical datasets, the method comprising: mining the database for pairs of entities that are indicated in the database as being associated with each other; for each pair of entities, determining a predicted ranking according to the method of any preceding claim; and determining an evaluation of the database using the predicted rankings.

Optionally, determining the evaluation comprises determining an average of the predicted rankings.

In a third aspect, the present disclosure provides a computer-implemented method of processing a database, the method comprising: mining the database for pairs of entities that are indicated in the database as being associated with each other; for each pair of entities, determining a predicted ranking according to the method of any of claims 1-12; and identifying pairs of entities having a predicted ranking outside a minimum standards range.

Optionally, the method comprises labelling the pairs of entities having a predicted ranking outside a minimum standards range. Optionally, the method comprises flagging for deletion or deleting the pairs of entities having a predicted ranking outside a minimum standards range.

In a fourth aspect, the present disclosure provides a computer-implemented method of optimising a classifier, the classifier comprising a set of rules comprising threshold values, the method comprising: inputting to the classifier one or more first scores each representing an extent of association between the entities of an entity pair, the extent of association being based on data mining on a respective one of one or more unstructured medical or scientific datasets; inputting to the classifier one or more second scores each representing an extent of association between the entities of the entity pair, the extent of association being based on data mining on a respective one of one or more structured medical or scientific datasets; using the classifier to determine a predicted ranking for the entity pair based on the one or more first scores and the one or more second scores; determining a loss between the predicted ranking and a reference ranking of the entity pair; and adjusting at least one of the threshold values of the set of rules to reduce the loss.

Optionally, the reference ranking comprises a manual ranking of the entity pair.

In a fifth aspect, the present disclosure provides a computer-implemented method of optimising a classifier, the classifier comprising a neural network, the method comprising: inputting to the classifier one or more first scores each representing an extent of association between the entities of an entity pair, the extent of association being based on data mining on a respective one of one or more unstructured medical datasets; inputting to the classifier one or more second scores each representing an extent of association between the entities of the entity pair, the extent of association being based on data mining on a respective one of one or more structured medical datasets; using the classifier to determine a predicted ranking for the entity pair based on the one or more first scores and the one or more second scores; and; training the neural network to minimise a loss between the predicted ranking and a reference ranking of the entity pair.

Optionally, the reference ranking comprises a manual ranking of the entity pair.

In a sixth aspect, the present disclosure provides a classifier optimised according to the computer-implemented method of the fourth aspect.

In a seventh aspect, the present disclosure provides a classifier optimised according to the computer-implemented method of the fifth aspect.

In an eighth aspect, the present disclosure provides a computer-readable medium comprising data or instruction code which, when executed on a processor, causes the processor to perform the computer-implemented method of any of the first to fifth aspects.

In a ninth aspect, the present disclosure provides a system for electronically mining medical and scientific datasets to determine a ranking indicating a level of evidence for an association between two entities, the system comprising: a user input module configured to receive a user input comprising a representation of an entity pair; a first data mining module configured to perform first data mining on one or more unstructured datasets to determine associations between the entities of the entity pair; a first scoring module configured to use the first data mining to generate one or more first scores each representing an extent of association between the entities of the entity pair and being based on a respective one of the one or more unstructured datasets; a second data mining module configured to perform second data mining on one or more structured datasets to determine associations between the entities of the entity pair; a second scoring module configured to use the second data mining to generate one or more second scores each representing an extent of association between the entities of the entity pair and being based on a respective one or the one or more unstructured datasets; a classifier configured to determine a predicted ranking for the entity pair using the one or more first scores and the one or more second scores; and a user output module configured to provide the predicted ranking to a user as an indication of the strength of evidence for an association between the entities of the entity pair.

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium. Examples of tangible (or non-transitory) storage media include disks, thumb drives, memory cards etc. and do not include propagated signals. The software can be suitable for execution on a parallel processor or a serial processor such that the method steps may be carried out in any suitable order, or simultaneously.

This application acknowledges that firmware and software can be valuable, separately tradable commodities. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

The optional features may be combined as appropriate, as would be apparent to a skilled person, and may be combined with any of the aspects of the invention.

BRIEF DESCRIPTION OF THE DRAWINGS

Embodiments of the invention will be described, by way of example, with reference to the following drawings, in which.

Figure 1:
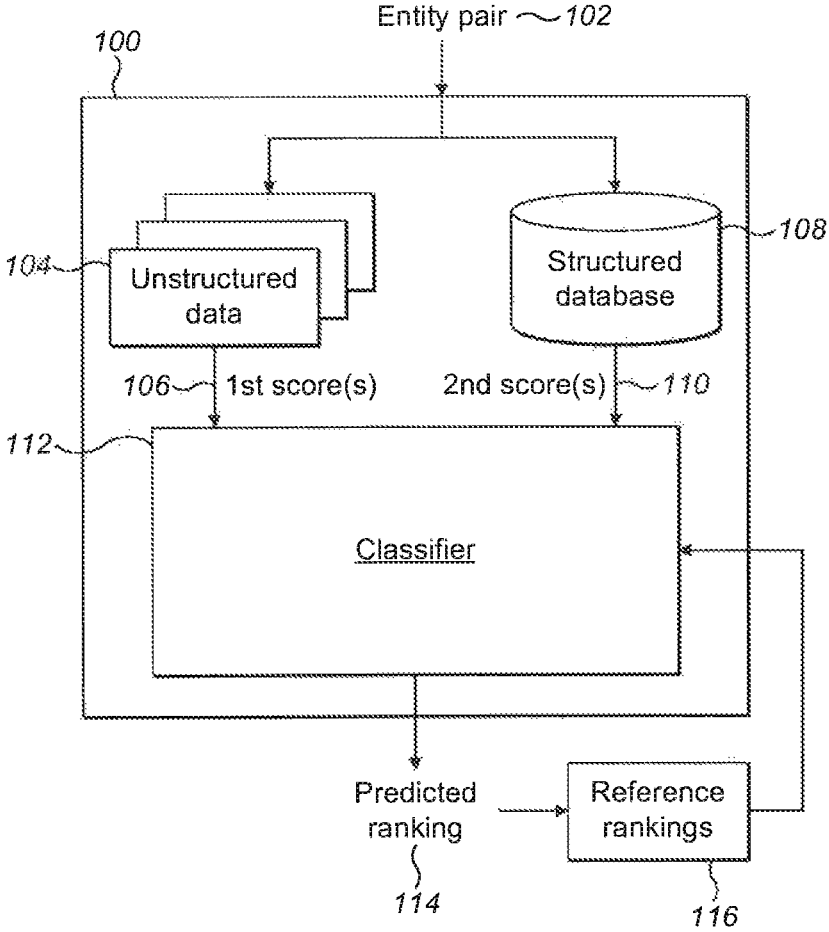
FIG. 1 is a schematic diagram illustrating a system for ranking an entity pair according to a level of literary evidence for an association between the two entities of the pair, in which the system comprises a classifier for determining the ranking.

Common reference numerals are used throughout the figures to indicate similar features.

DETAILED DESCRIPTION

Embodiments of the present invention are described below by way of example only. These examples represent the best ways of putting the invention into practice that are currently known to the Applicant although they are not the only ways in which this could be achieved. The description sets forth the functions of the example and the sequence of steps for constructing and operating the example. However, the same or equivalent functions and sequences may be accomplished by different examples.

FIG. 1 illustrates a system 100 for electronically mining medical and scientific datasets to determine a ranking for a pair of entities. In order to assist and support drug discovery scientists in identifying new avenues of research, the ranking represents a level of evidence in the literature for an association between the entities of the pair, so that entity pairs with middling levels of evidence, and consequently some research potential, can be more easily identified.

The system 100 is configured to receive a representation 102 of an entity pair and to predict a ranking that indicates the strength of evidence in the literature for an association between the entities of the pair. This is achieved by mining data from both structured and unstructured datasets, and by generating scores from each dataset which can be used as an input for predicting the ranking.

Referring to FIG. 1, the system 100 is configured to mine one or more unstructured datasets 104 to determine associations between the entities of the entity pair, and to generate one or more first scores 106 each representing an extent of association between the entities of the entity pair. Each of the one or more unstructured datasets 104 may or may not be part of the system 100, and in many suitable embodiments they are external datasets with which the system 100 is communicatively connected at least to the extent that the data mining by the system 100 is possible.

The unstructured datasets 104 may for example comprise at least one of medical research papers, scientific research papers and patents. The mining of the unstructured datasets 104 may comprise performing a suitable text recognition process such as natural language processing or named entity recognition.

These techniques can be used to generate the first scores 106 which provide counts or statistical indications of co-occurrences of the entities of the pair in the literature. For example, the first scores 106 may comprise one or more of a number of sentences mentioning both entities of the pair (sentences with pair co-occurrences), an 'SLPs' score denoting a number of sentences in which the pair is syntactically linked, a number of papers containing sentences in which the pair is syntactically linked (an 'SLPp' score), and an area under an SLP curve (an 'AUS' score.) Although 'AUS' stands for an area under a curve, the AUS score actually represents a normalised SLP curve based on a raw frequency of one of the entities of the pair. As such, the AUS score may also be referred to as a 'normalised SLP score' and provides an indication of how frequently a pair is syntactically linked in literature beyond what could be expected from chance alone. An 'SLP score' refers to either an SLPs score or an SLPp score. The first scores 106 may additionally or alternatively comprise one or more other normalised co-occurrence or syntactically linked pair counts, or a number of co-occurrences or syntactically linked pairs with additional predetermined words setting additional constraints such as requiring that the pair is linked in another way such as by specific assay or in a specific species.

As indicated above, the system 100 is configured to mine data from both structured and unstructured datasets, and as such is configured to mine at least one structured database 108 to determine associations between the entities of the entity pair, and to generate one or more second scores 110 each representing an extent of association between the entities of the entity pair. The at least one structured dataset 108 may or may not be part of the system 100, and in many suitable embodiments it comprises an external dataset with which the system 100 is communicatively connected at least to the extent that the data mining by the system 100 is possible.

The at least one structured dataset 108 may for example comprise a biomedical database such as Online Mendelian Inheritance in Man (OMIM) which contains relationships between, among other things, diseases and human gene or target entities. Additionally or alternatively, the at least one structured dataset 108 may comprise a database of clinical trial data such as the clinical trial dataset available at ClinicalTrials.gov which documents the clinical trial phases for compounds in diseases and can be associated with targets. The mining of the at least one structured dataset 108 may comprise various actions such as a simple look up operation. For example, in the case of OMIM, it is possible to look up a disease entity and retrieve an associated gene or target entity.

These actions can be used to generate the second scores 110 which provide scores, values or other data retrieved from the at least one structured database 108. For example, the second scores 110 may comprise one or more of clinical trial phase data, categorisation of a type of relationship between the entities of the pair, a phase II clinical trial success rating, and a phase IV drug or genetic association score for the entity pair. In an example, the genetic association score may be based on a genetic association in humans from Genome Wide Association Studies. The second scores 110 may additionally or alternatively comprise a status of 'reduced to practice' meaning that a target has been modulated in a disease model and has been shown to affect the disease phenotype, or may additionally or alternatively be based on a comparison between annotations of the entities of the pair. Another possible conclusion from mining a structured database may comprise and indication that there has been no clinical trial. This may be of use if combined with a result that there is some association between entities of a pair from unstructured data in literature.

It will be appreciated that the entity pair may suitably comprise two biological entities, as may be found in medical and scientific literature and as may be of interest to the drug discovery scientist. Biological entities include entities such as drugs, compounds, diseases, biological mechanisms, biological pathways, genes, other nucleic acids, cell types, tissue types, and proteins. In the case that the entity pair comprises at least one biological entity, the at least one biological entity may comprise a disease, and the entity pair may comprise a disease-target pair. In this context, a target is a biological entity that may be, or that potentially may be, targeted by a compound, ligand, drug, or cell therapy approach. As such, a target may for example comprise a gene, other nucleic acid, protein or other biological entity.

As outlined above, the system 100 is configured to output a ranking for the entity pair. With reference to FIG. 1, the system 100 is configured to use a classifier 112 to determine a predicted ranking 114 for the entity pair using the one or more first scores 106 and the one or more second scores 110, and to provide the predicted ranking 114 to a user as an indication of the strength of evidence for an association between the entities of the entity pair. The classifier 112 may be optimised using reference rankings 116 as described below.

Figure 2:
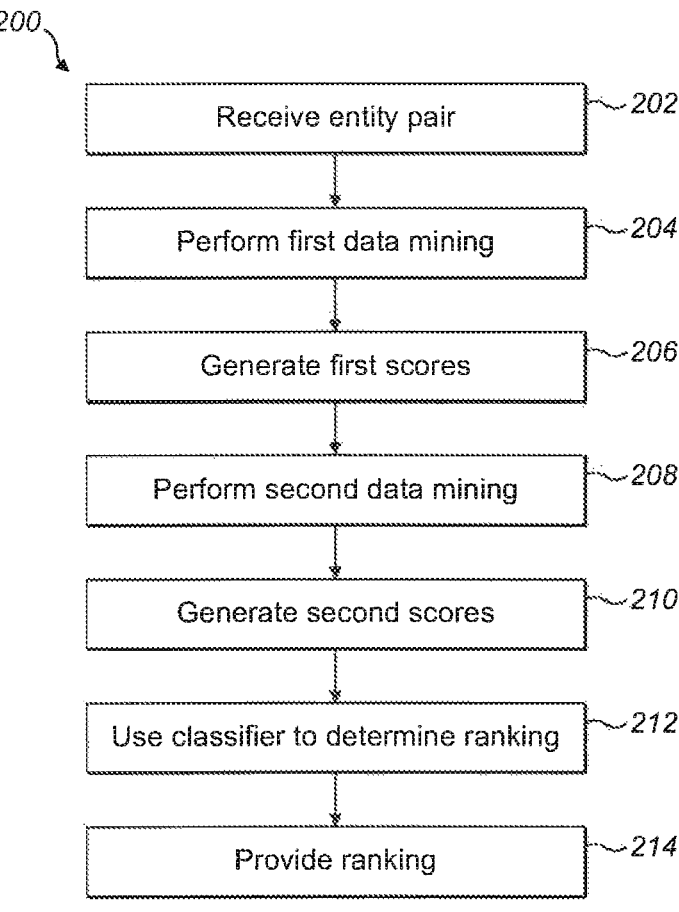
FIG. 2 is a flow chart illustrating a method of electronically mining medical and scientific datasets to determine a ranking indicating a level of evidence for an association between two entities.

With reference to FIG. 2, a computer-implemented method 200 of electronically mining medical and scientific datasets to determine a ranking indicating a level of evidence for an association between two entities is disclosed. The method 200 comprises: receiving 202 a representation of an entity pair; performing 204 first data mining on one or more unstructured datasets to determine associations between the entities of the entity pair; using the first data mining to generate 206 one or more first scores each representing an extent of association between the entities of the entity pair and being based on a respective one of the one or more unstructured datasets; performing 208 second data mining on one or more structured datasets to determine associations between the entities of the entity pair; using the second data mining to generate 210 one or more second scores each representing an extent of association between the entities of the entity pair and being based on a respective one of the one or more structured datasets; using 212 a classifier to determine a predicted ranking for the entity pair using the one or more first scores and the one or more second scores; and providing 214 the predicted ranking to a user as an indication of the strength of evidence for an association between the entities of the entity pair.

Figure 3:
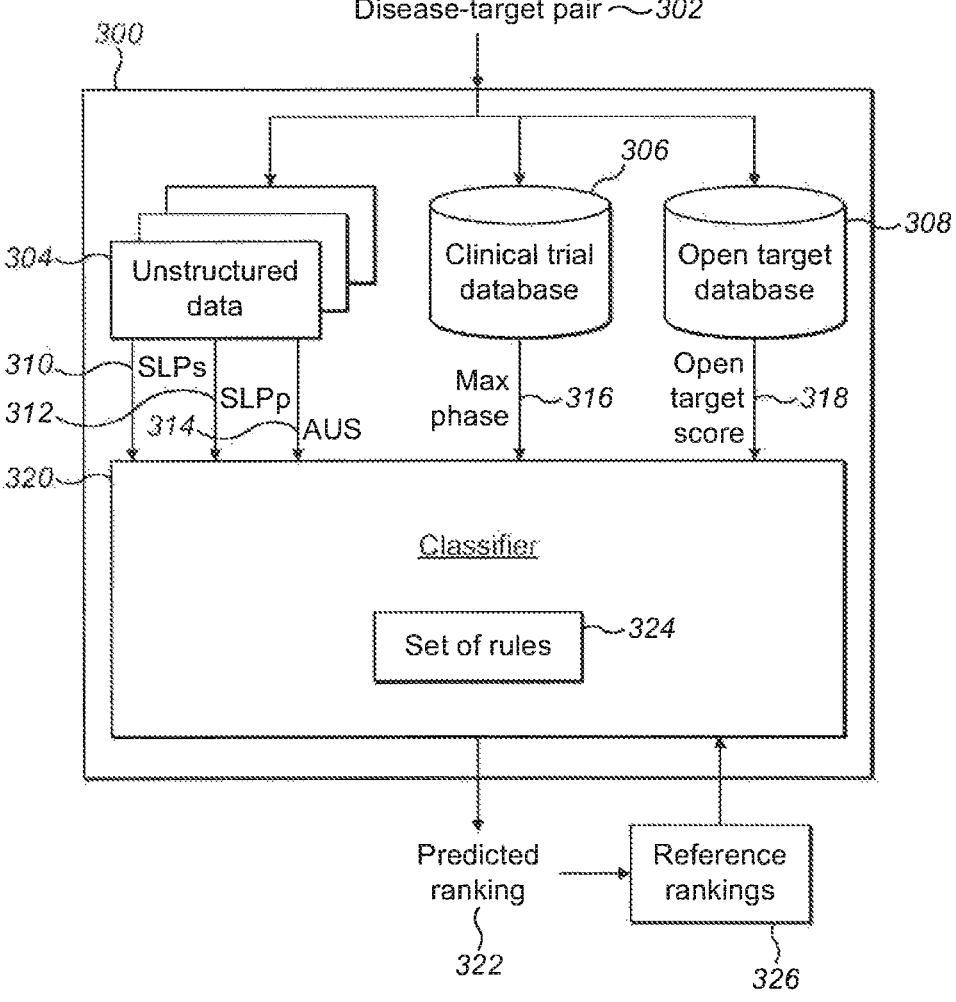
FIG. 3 is a schematic diagram illustrating a system for ranking a disease-target pair according to a level of literary evidence for an association between the two entities of the pair, in which the system comprises a classifier having a set of rules for determining the ranking.

Referring to FIG. 3, system 300 provides an example of system 200. The system 300 is configured to receive a representation 302 of a disease-target pair and to mine data from an unstructured dataset 304, a clinical trial database 306 and an open target database 308. The system 300 generates an SLPs score 310, an SLPp score 312 and an AUS score 314 by mining the unstructured dataset 304; a maximum phase 316 by mining the clinical trial database 306; and an open target score 318 by mining the open target database 308. The maximum phase 316 represents a maximum clinical trial phase achieved for the disease-target pair as annotated in structured clinical trial databases. The open target score 318 comprises a score from the Open Targets Platform and database.

The system 300 comprises a classifier 320 configured to receive the scores 310-318 and to determine a predicted ranking 322 using the scores 310-318. In the example of system 300, the classifier 320 comprises a set of rules 324 for determining the predicted ranking 322, and as will be described below the set of rules 324 may be optimised using a set of reference rankings 326.

The set of rules 324 functions to determine which ranking of a set of discrete rankings should be assigned to each entity pair. Since the classifier uses the scores 310-318 to determine a predicted ranking, the predicted ranking is based on scores from both unstructured data 304 and structured datasets 306, 308. The set of rules 324 provides a deterministic set of criteria for each entity pair that will lead to a unique ranking being assigned.

The set of rules 324 may comprise at least one threshold value for one or more of the first scores from unstructured data 310, 312, 314 and/or for one or more of the second scores from structured data 316, 318. For example, the set of rules 324 may comprise upper and/or lower bounds on counts, scores or other statistics relating to co-occurrence or syntactically linked co-occurrences of the entities of the entity pair in sentences or papers in the unstructured data 304. The set of rules 324 may also comprise required categorisations or annotations in structured data 306, 308. For example, the set of rules 324 may require that the entities of the entity pair are associated with at least one Phase III clinical trial, as indicated in a clinical trial database. In another example, the set of rules 324 may require that the entities of the entity pair have a score greater than 0.5 in the Open Targets Platform database for genetic association. A grouping of such rules together enable the classifier 320 to categories each disease-target pair into a deterministic, discrete ranking.

In an example set of rankings, the following four possible rankings can be assigned to a disease-target pair:
(1) passed phase II clinical trials
(2) reduced to practice or strong evidence
(3) some literature evidence
(4) little or no evidence In this case, the set of rules 324 may be arranged to assign a ranking of 1 to a disease-target pair that has passed phase II clinical trials and has a high AUS or open target score. Rankings of 2 and 3 may be assigned for middling values for the SLP, AUS and open target scores and middling requirements for clinical trial data. A ranking of 4 may be characterised by a null value for the clinical trial data (meaning no data is available), a null value for the open target score (meaning no data is available), and SLP and AUS scores being below certain thresholds.

Figure 4:
FIG. 4 is a table illustrating an example set of rules for determining a ranking.

An example set of rules 400 arranged in this way is shown in FIG. 4. For each of the four above rankings 1-4, criteria 402 are shown which must be satisfied by the scores 310-318 in order for a disease-target pair to be assigned that ranking.

For example, in order to be assigned a ranking of 1, a disease-target pair must have achieved success in phase 2 clinical trials, as determined by the mining of the clinical trial database 306, and must also have achieved either an AUS score of more than 0.5 or an open target score of more than 0.7.

In order to be assigned a ranking of 2, a disease-target pair must be reduced to practice, and must also have achieved an SLPs score of at least 200, an SLPp score of at least 100, an AUS score of at least 0.35 and an open target score of 1. Finally, in order to be assigned a ranking of 2, a disease-target pair must not have scores satisfying the criteria for a ranking of 1.

To be assigned a ranking of 3, a disease-target pair must have clinical trial data that is not null (where 'null' means that no data is available), and must also have an SLPs score of at least 6, an SLPp score of at least 1, an AUS score of at least 0.05, and an open target score between 0 and 1. To receive a ranking of 3, the disease-target pair must also not have scores satisfying the criteria for a ranking of 1 or 2.

Any disease-target pair having scores that do not satisfy the criteria for rankings 1, 2 or 3 is assigned a ranking of 4.

The threshold values stipulated in the set of rules 400 may be optimised by iterative comparison with training data to ensure that the classifier 320 is able to make accurate and valuable predictions of rankings.

Figure 5:
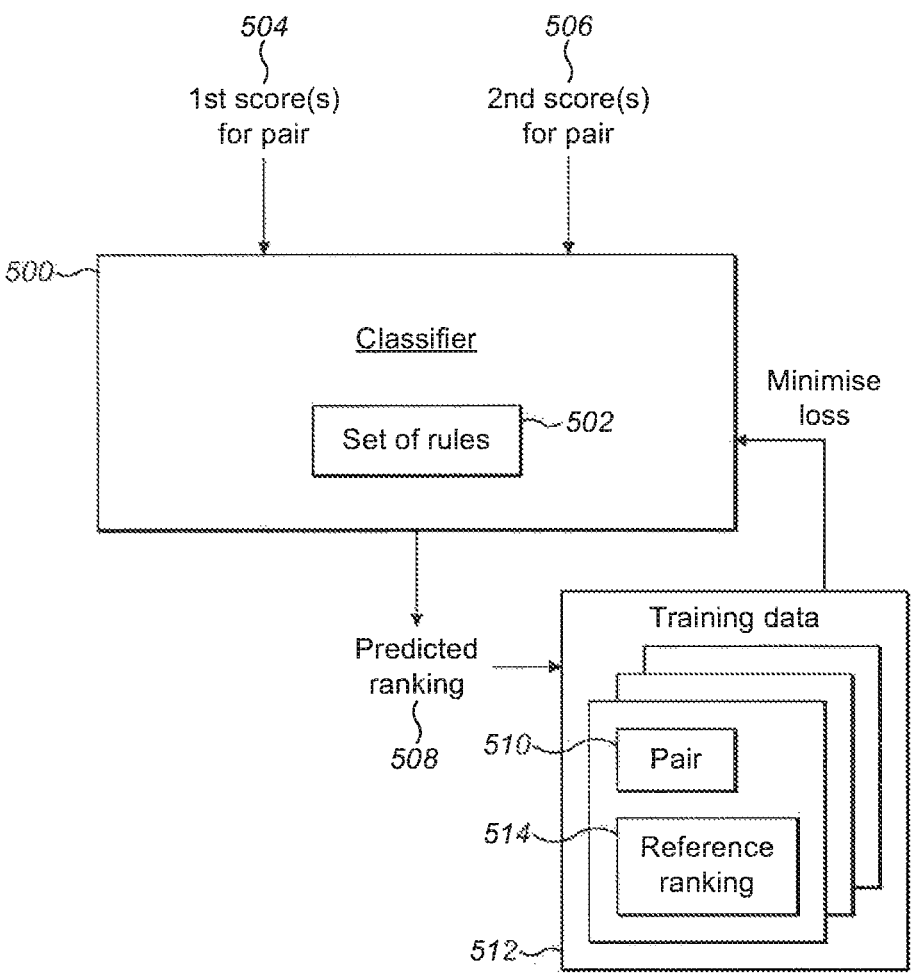
FIG. 5 is a schematic diagram illustrating a system for optimising threshold values of the set of rules.

A classifier 500 optimised in this way is shown in FIG. 5. The classifier 500 comprises a set of rules 502 comprising threshold values for determining a predicted ranking for an entity pair, and is configured to receive one or more first scores 504 and one or more second scores 506 for the entity pair. The scores 504, 506 each represent an extent of association between the entities of the entity pair based on whichever one or more datasets that were used to generate them. The first scores 504 are based on data mining from one or more unstructured medical or scientific datasets and the second scores 506 are based on data mining from one or more structured medical or scientific datasets.

The set of rules 502 is optimised by iteratively optimising the threshold values of the rules. In a first iteration, the set of rules starts with an initial set of threshold values, for example manually selected by a drug discovery scientist based on his or her knowledge of the field. The classifier 500 is then used to determine a predicted ranking 508 for the entity pair based on the one or more first scores 504 and the one or more second scores 506. In this optimisation process, the entity pair 510 belongs to a set of training data 512 for which a reference ranking 514 is already known. The reference ranking 514 is an optimum ranking which may comprise a manual ranking of the entity pair, for example by a drug discovery scientist. The classifier 500 is optimised by determining a loss between the predicted ranking 508 and the reference ranking 514 and adjusting at least one of the threshold values of the set of rules 502 to reduce the loss. As this iterative process is repeated, the threshold values of the set of rules 502 tend toward optimum values that cause the classifier 500 to predict rankings in such a way as to conform increasingly closely with the reference rankings 514 of the training data 512.

The at least one threshold value may be optimised using a range of suitable techniques known to the engineer in the field, for example a statistical optimisation method or a machine learning algorithm. If a machine learning algorithm is used, this may suitably comprise a random forest algorithm, for example.

Figure 6:
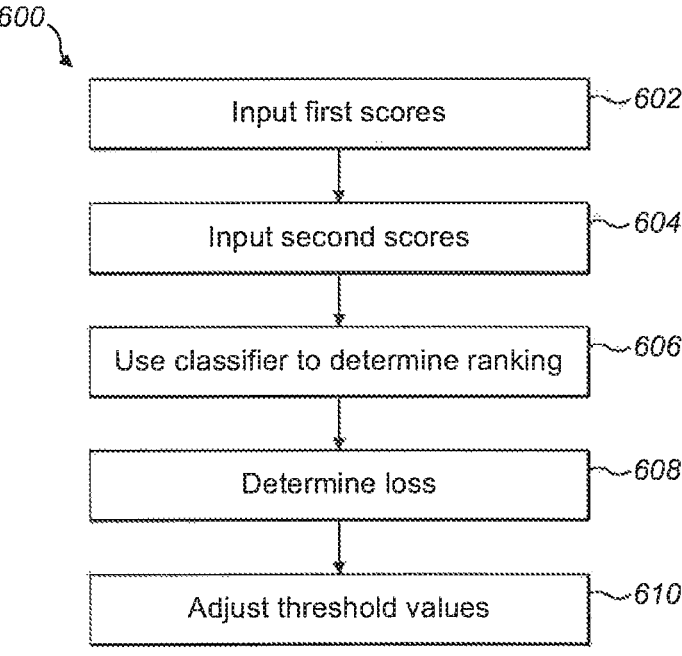
FIG. 6 is a flow chart illustrating a method of optimising a classifier, the classifier being configured to rank entity pairs and comprising a set of rules comprising threshold values.

With reference to FIG. 6, a computer-implemented method 600 of optimising a classifier, the classifier comprising a set of rules comprising threshold values, is disclosed. The method 600 comprises inputting 602 to the classifier one or more first scores each representing an extent of association between the entities of an entity pair, the extent of association being based on data mining on a respective one of one or more unstructured medical or scientific datasets; inputting 604 to the classifier one or more second scores each representing an extent of association between the entities of the entity pair, the extent of association being based on data mining on a respective one of one or more structured medical or scientific datasets; using 606 the classifier to determine a predicted ranking for the entity pair based on the one or more first scores and the one or more second scores; determining 608 a loss between the predicted ranking and a reference ranking of the entity pair; and adjusting 610 at least one of the threshold values of the set of rules to reduce the loss.

Figure 7:
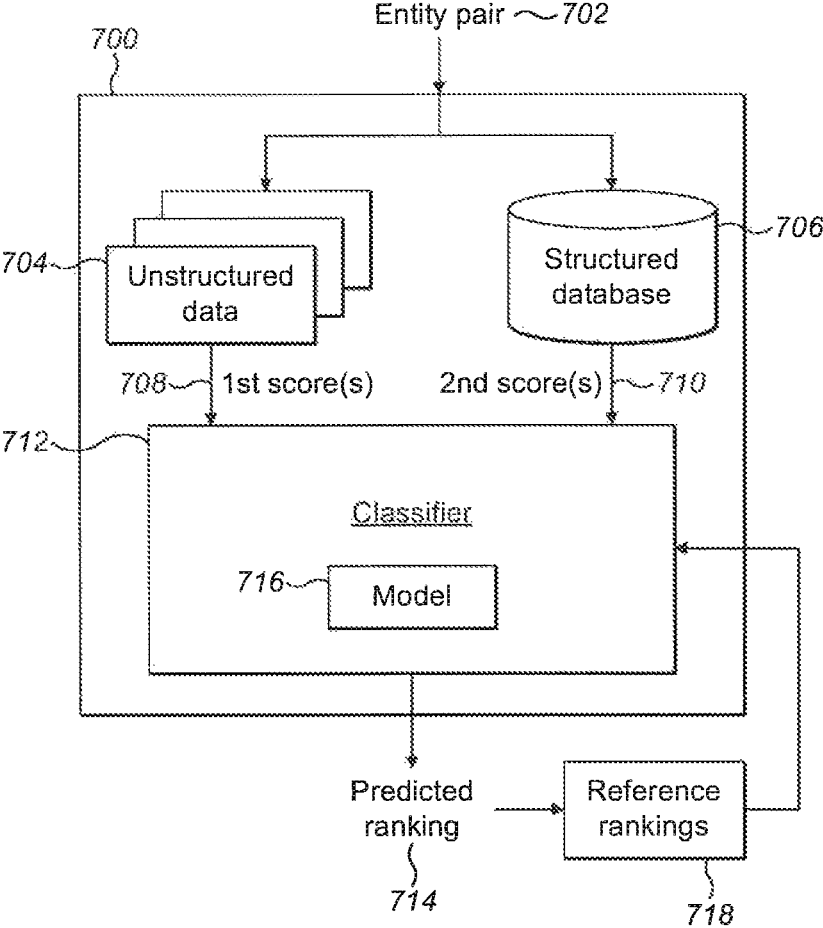
FIG. 7 is a schematic diagram illustrating a system for ranking an entity pair according to a level of literary evidence for an association between the two entities of the pair, in which the system comprises a classifier having a neural network for determining the ranking.

Referring to FIG. 7, system 700 provides an example of system 200. The system 700 is configured to receive a representation 702 of an entity pair such as a disease-target pair and to mine data from an unstructured dataset 702, and a structured database 706 such as a clinical trial database or an open target database. The system 700 generates one or more first scores 708 by mining the unstructured dataset 704 and one or more second scores 710 by mining the structured database 706. The scores 708, 710 each represent an extent of association between the entities of the entity pair 702, in a similar way to the scores described above in relation to FIGS. 1 and 3.

The system 700 comprises a classifier 712 configured to receive the scores 708, 710 and to determine a predicted ranking 714 using the scores 708, 710. In the example of system 700, the classifier 712 comprises a model 716 for determining the predicted ranking 714, and may be trained using training data comprising reference rankings 718. Suitably, the reference rankings 718 may comprise manually ranked entity pairs, for example prepared by a drug discovery scientist.

The model 712 functions to determine which ranking of a set of discrete rankings should be assigned to each entity pair. Since the model 716 uses the scores 708, 710 to determine a predicted ranking 714, the predicted ranking 714 is based on scores from both unstructured data 704 and structured datasets 706. The model 716 provides a deterministic set of criteria for each entity pair that will lead to a unique ranking being assigned. In suitable examples, the model 716 comprises a machine learning algorithm such as a neural network. If the model 716 comprises a machine learning model, this may suitably comprise a random forest algorithm, a decision tree model, or a neural network model. In other examples, the model 716 may utilise other multi-class supervised classification methods or even unsupervised classification methods.

Figure 8:
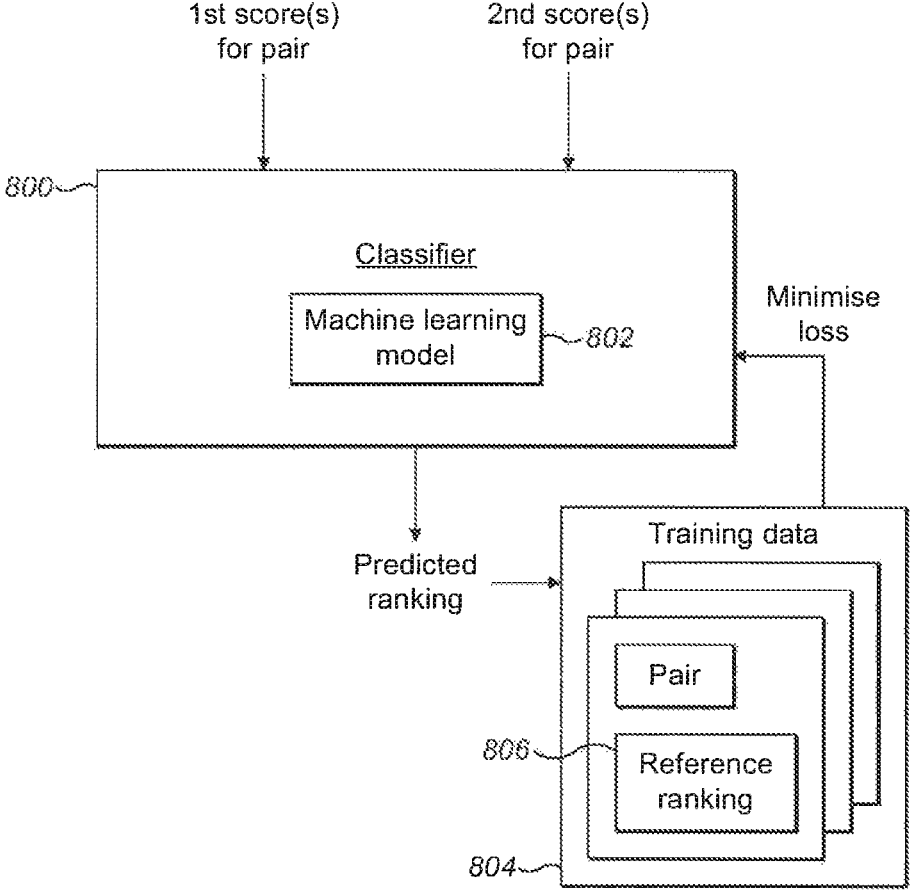
FIG. 8 is a schematic diagram illustrating a system for training the neural network.

Referring to FIG. 8, a classifier 800 comprising a machine learning model 802 may be trained to predict rankings based on training data 804 comprising reference rankings 806. In suitable examples, the reference rankings 806 comprise manually ranked entity pairs.

Figure 9:
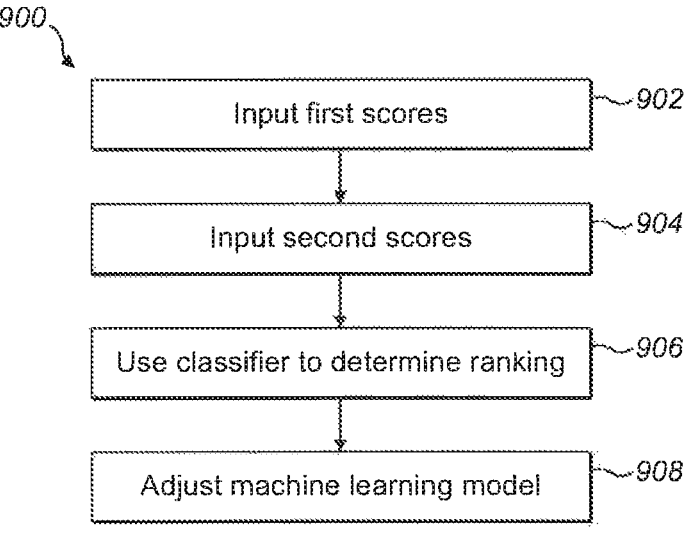
FIG. 9 is a flow chart illustrating a method of optimising a classifier, the classifier being configured to rank entity pairs and comprising a neural network.

With reference to FIG. 9, a computer-implemented method 900 of optimising a classifier, the classifier comprising a model such as a neural network, is disclosed. The method 900 comprises: inputting 902 to the classifier one or more first scores each representing an extent of association between the entities of an entity pair, the extent of association being based on data mining on a respective one of one or more unstructured medical datasets; inputting 904 to the classifier one or more second scores each representing an extent of association between the entities of the entity pair, the extent of association being based on data mining on a respective one of one or more structured medical datasets; using 906 the classifier to determine a predicted ranking for the entity pair based on the one or more first scores and the one or more second scores; and adjusting 908 the model to minimise a loss between the predicted ranking and a reference ranking of the entity pair. The method 900 may be repeated for further first and second scores relating to other entity pairs as part of an iterative process to train the model.

The above systems 100, 300, 700 and methods 200, 600, 900 for determining a predicted ranking for an entity pair may be used to process a database, for example to evaluate or cleanse the database. Databases to which this can be applied store data indicating associations between pairs of entities, and in this approach the above techniques can be used to verify whether these associations are correct.

In the case of database evaluation, the above techniques may be used to determine a predicted ranking for each pair of entities that is indicated in a database as being associated with each other. An evaluation may then be determined based on the predicted rankings, for example by determining an average of the predicted rankings. The evaluation may provide an indication of the quality and reliability of the database as a whole and may therefore be used to assess and compare the quality of available public, commercial or other databases of interest. The evaluation may also provide a guide for identifying databases that are valuable for a specific use, such as databases listing entity pairs with middling predicted rankings that indicate research potential.

In the case of database cleansing, the above techniques may also be used to determine a predicted ranking for each pair of entities that is indicated in a database as being associated with each other. In this case, any of the pairs of entities that have a predicted ranking outside a required range may be identified, and optionally flagged for deletion or for evaluation by a human. The identified entity pairs may also be automatically deleted from the database for database cleansing. This approach may be useful in quality control for imposing minimum standards on a database. In an alternative approach, pairs of entities that have a predicted ranking outside a required range may be labelled. This enables the labelled pairs to be excluded from any downstream analysis of the data in the database whilst keeping the database intact.

Figure 10:
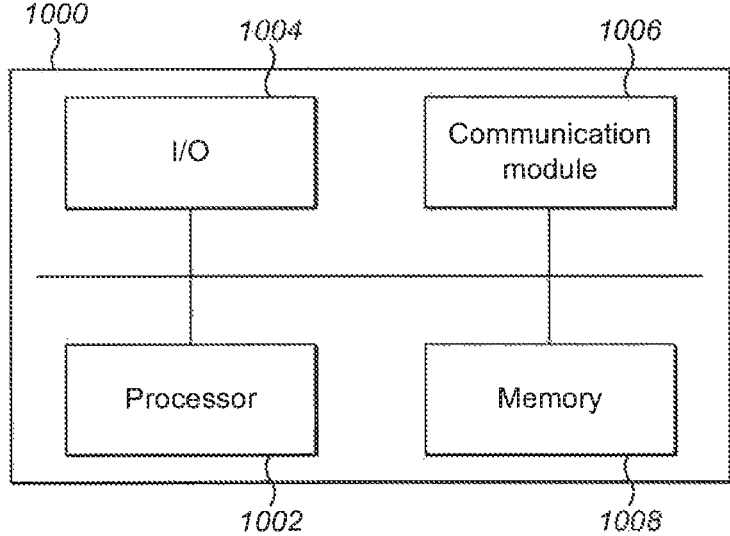
FIG. 10 is a schematic diagram illustrating suitable hardware for implementing methods according to the present disclosure.

Referring to FIG. 10, the above disclosed methods and techniques may be implemented using hardware 1000. The hardware 1000 includes a processor 1002, an input/output device 1004, a communications module 1006, and memory 1008. The memory 1008 may store a program that when executed causes the processor 1002 to implement any of the above disclosed methods, for example methods 200, 600 and 900.

In the embodiment described above the server may comprise a single server or network of servers. In some examples the functionality of the server may be provided by a network of servers distributed across a geographical area, such as a worldwide distributed network of servers, and a user may be connected to an appropriate one of the network of servers based upon a user location.

The above description discusses embodiments of the invention with reference to a single user for clarity. It will be understood that in practice the system may be shared by a plurality of users, and possibly by a very large number of users simultaneously.

The embodiments described above are fully automatic. In some examples a user or operator of the system may manually instruct some steps of the method to be carried out.

In the described embodiments of the invention the system may be implemented as any form of a computing and/or electronic device. Such a device may comprise one or more processors which may be microprocessors, controllers or any other suitable type of processors for processing computer executable instructions to control the operation of the device in order to gather and record routing information. In some examples, for example where a system on a chip architecture is used, the processors may include one or more fixed function blocks (also referred to as accelerators) which implement a part of the method in hardware (rather than software or firmware). Platform software comprising an operating system or any other suitable platform software may be provided at the computing-based device to enable application software to be executed on the device.

Various functions described herein can be implemented in hardware, software, or any combination thereof. If implemented in software, the functions can be stored on or transmitted over as one or more instructions or code on a computer-readable medium. Computer-readable media may include, for example, computer-readable storage media. Computer-readable storage media may include volatile or non-volatile, removable or non-removable media implemented in any method or technology for storage of information such as computer readable instructions, data structures, program modules or other data. A computer-readable storage media can be any available storage media that may be accessed by a computer. By way of example, and not limitation, such computer-readable storage media may comprise RAM, ROM, EEPROM, flash memory or other memory devices, CD-ROM or other optical disc storage, magnetic disc storage or other magnetic storage devices, or any other medium that can be used to carry or store desired program code in the form of instructions or data structures and that can be accessed by a computer. Disc and disk, as used herein, include compact disc (CD), laser disc, optical disc, digital versatile disc (DVD), floppy disk, and blu-ray disc (BD). Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, DSL, or wireless technologies such as infrared, radio, and microwave are included in the definition of communication medium. Combinations of the above should also be included within the scope of computer-readable media.

Alternatively, or in addition, the functionality described herein can be performed, at least in part, by one or more hardware logic components. For example, and without limitation, hardware logic components that can be used may include Field-programmable Gate Arrays (FPGAs), Program-specific Integrated Circuits (ASICs), Program-specific Standard Products (ASSPs), System-on-a-chip systems (SOCs). Complex Programmable Logic Devices (CPLDs), etc.

Although illustrated as a single system, it is to be understood that the computing device may be a distributed system. Thus, for instance, several devices may be in communication by way of a network connection and may collectively perform tasks described as being performed by the computing device.

Although illustrated as a local device it will be appreciated that the computing device may be located remotely and accessed via a network or other communication link (for example using a communication interface).

The term 'computer' is used herein to refer to any device with processing capability such that it can execute instructions. Those skilled in the art will realise that such processing capabilities are incorporated into many different devices and therefore the term 'computer' includes PCs, servers, mobile telephones, personal digital assistants and many other devices.

Those skilled in the art will realise that storage devices utilised to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realise that by utilising conventional techniques known to those skilled in the art that all, or a portion of the software instructions may be carried out by a dedicated circuit, such as a DSP, programmable logic array, or the like.

It will be understood that the benefits and advantages described above may relate to one embodiment or may relate to several embodiments. The embodiments are not limited to those that solve any or all of the stated problems or those that have any or all of the stated benefits and advantages.

Any reference to 'an' item refers to one or more of those items. The term 'comprising' is used herein to mean including the method steps or elements identified, but that such steps or elements do not comprise an exclusive list and a method or apparatus may contain additional steps or elements.

As used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices.

Further, as used herein, the term "exemplary" is intended to mean "serving as an illustration or example of something".

Further, to the extent that the term "includes" is used in either the detailed description or the claims, such term is intended to be inclusive in a manner similar to the term "comprising" as "comprising" is interpreted when employed as a transitional word in a claim.

The figures illustrate exemplary methods. While the methods are shown and described as being a series of acts that are performed in a particular sequence, it is to be understood and appreciated that the methods are not limited by the order of the sequence. For example, some acts can occur in a different order than what is described herein. In addition, an act can occur concurrently with another act. Further, in some instances, not all acts may be required to implement a method described herein.

Moreover, the acts described herein may comprise computer-executable instructions that can be implemented by one or more processors and/or stored on a computer-readable medium or media. The computer-executable instructions can include routines, sub-routines, programs, threads of execution, and/or the like. Still further, results of acts of the methods can be stored in a computer-readable medium, displayed on a display device, and/or the like.

The order of the steps of the methods described herein is exemplary, but the steps may be carried out in any suitable order, or simultaneously where appropriate. Additionally, steps may be added or substituted in, or individual steps may be deleted from any of the methods without departing from the scope of the subject matter described herein. Aspects of any of the examples described above may be combined with aspects of any of the other examples described to form further examples without losing the effect sought.

It will be understood that the above description of a preferred embodiment is given by way of example only and that various modifications may be made by those skilled in the art. What has been described above includes examples of one or more embodiments. It is, of course, not possible to describe every conceivable modification and alteration of the above devices or methods for purposes of describing the aforementioned aspects, but one of ordinary skill in the art can recognize that many further modifications and permutations of various aspects are possible. Accordingly, the described aspects are intended to embrace all such alterations, modifications, and variations that fall within the scope of the appended claims.

The invention claimed is:

1. A computer-implemented method of determining a biological entity pair of interest for drug discovery by electronically mining medical and scientific datasets to determine a ranking indicating a strength of evidence for an association between two biological entities, the method comprising:

receiving, by a server, a representation of a biological entity pair;

generating, by the server, one or more first scores each representing an extent of association between the entities of the biological entity pair by performing first data mining on one or more unstructured datasets;

generating, by the server, one or more second scores each representing an extent of an association between the entities of the biological entity pair by performing second data mining on one or more structured datasets;

receiving, by a trained machine learning model from the server, the one or more first scores and the one or more second scores;

using the trained machine learning model to determine a predicted ranking for the entity pair using the one or more first scores and the one or more second scores, wherein the trained machine learning model is trained to assign the predicted ranking from a set of possible discrete rankings by applying a set of rules comprising at least one threshold value applied to the one or more first scores and to the one or more second scores and grouping the set of rules to determine the predicted ranking, wherein the predicted ranking is a discrete ranking from the set of possible discrete rankings;

determining, by the trained machine learning model, a loss between the predicted ranking and a reference ranking for the entity pair;

iteratively adjusting, by the trained machine learning model, the at least one threshold value to reduce the loss between the predicted ranking and a reference ranking for the entity pair;

updating the trained machine learning model based on the adjusted at least one threshold value;

using the updated trained machine learning model to determine an updated predicted ranking for the entity pair;

displaying, by the trained machine learning model, to a user, an indication of the strength of evidence for the association between the entities of the biological entity pair based on the updated predicted ranking; and identifying a biological entity pair of interest based on the updated predicted ranking.

2. The computer-implemented method of claim 1, wherein each entity of the biological entity pair comprises a drug, a compound, a disease, a biological mechanism, a biological pathway, a gene, another nucleic acid, a cell type, a tissue type, or a protein.

3. The computer-implemented method of claim 1, wherein each of the one or more first scores is based on a respective one of the one or more unstructured datasets and/or each of the one or more second scores is based on a respective one of the one or more structured datasets.

4. The computer-implemented method of claim 1, wherein the one or more first scores comprises at least one of an SLP score and an AUS score.

5. The computer-implemented method of claim 1, wherein the one or more second scores comprise at least one of a phase II clinical trial success rating or a phase IV drug or genetic association score for the biological entity pair.

6. The computer-implemented method of claim 1, wherein the at least one threshold value is optimised using manually ranked biological entity pairs.

7. The computer-implemented method of claim 1, wherein the at least one threshold value is optimised using a statistical optimisation method or a machine learning model.

8. The computer-implemented method of claim 1, wherein the trained machine learning model comprises a neural network.

9. The computer-implemented method of claim 1, wherein the trained machine learning model is trained using manually ranked biological entity pairs.

10. A computer-implemented method of evaluating a database with respect to medical datasets, the method comprising:

mining the database for pairs of biological entities that are indicated in the database as being associated with each other;

for each pair of biological entities, determining a predicted ranking according to the method of claim 1; and determining an evaluation of the database using the predicted rankings.

11. The computer-implemented method of claim 10, wherein determining the evaluation comprises determining an average of the predicted rankings.

12. A computer-implemented method of processing a database, the method comprising:

mining the database for pairs of biological entities that are indicated in the database as being associated with each other;

for each pair of biological entities, determining a predicted ranking according to the method of claim 1; and identifying pairs of biological entities having a predicted ranking outside a minimum standards range.

13. The computer-implemented method of claim 12, comprising labelling the pairs of biological entities having a predicted ranking outside a minimum standards range.

14. The computer-implemented method of claim 12, comprising flagging for deletion or deleting the pairs of biological entities having a predicted ranking outside a minimum standards range.

15. A non-transitory computer-readable medium comprising data or instruction code which, when executed on a processor, causes the processor to perform the computer-implemented method of claim 1.

16. A system for electronically mining medical and scientific datasets to determine a biological entity pair of interest for use in drug discovery by determining a ranking indicating a strength of evidence for an association between two biological entities, the system comprising:

an input device configured to receive a user input comprising a representation of a biological entity pair;

a processor operably connected to the input device and configured to execute operations including:

performing first data mining on one or more unstructured datasets to determine associations between the entities of the biological entity pair;

generating one or more first scores each representing an extent of association between the entities of the biological entity pair and being based on a respective one of the one or more unstructured datasets and the first data mining;

performing second data mining on one or more structured datasets to determine associations between the entities of the biological entity pair;

generating one or more second scores each representing an extent of association between the entities of the biological entity pair and being based on a respective one or the one or more structured datasets and the second data mining;

using trained machine learning model to receive the one or more first scores and the one or more second scores;

using the trained machine learning model to determine a predicted ranking for the entity pair using the one or more first scores and the one or more second scores, wherein the trained machine learning model is configured to assign the predicted ranking from a set of possible discrete rankings by applying a set of rules comprising at least one threshold value applied to the one or more first scores and to the one or more second scores and grouping the set of rules to determine the predicted ranking, wherein the predicted ranking is a discrete ranking from the set of possible discrete rankings;

comparing, by the trained machine learning model, the predicted ranking to a reference ranking, wherein the reference ranking is an optimum ranking for the entity pair;

iteratively adjusting, by the trained machine learning model, the at least one threshold value based on the comparison of the predicted ranking and the reference ranking to reduce a loss between the predicted ranking and the reference ranking; and updating the trained machine learning model based on the adjusted at least one threshold value;

using the updated trained machine learning model to determine an updated predicted ranking for the entity pair; and an output device operably coupled to the processor and configured to output the indication of the strength of evidence for an association between the entities of the biological entity pair and an indication of the biological entity pair of interest based on the updated predicted ranking.

17. The computer-implemented method of claim 4, wherein the one or more unstructured datasets comprises at least one of medical or scientific literature.

18. The computer-implemented method of claim 5, wherein the one or more structured datasets comprises a database of clinical trial data.

19. The computer-implemented method of claim 8, further comprising:

training the neural network using the predicted ranking and a reference ranking of the biological entity pair.

20. The computer-implemented method of claim 1, further comprising using the biological entity pair of interest in drug discovery.

21. The system of claim 16, wherein:

the one or more unstructured datasets comprises at least one of medical or scientific literature;

the one or more structured datasets comprises a database of clinical trial data;

the one or more first scores comprises at least one of an SLP score or an AUS score; and the one or more second scores comprises at least one of a phase II clinical trial success rating or a phase IV drug or genetic association score for the biological entity pair.

22. The computer-implemented method of claim 1, wherein the one or more first scores comprise at least one of an SLP score or an AUS score and the one or more second scores comprise at least one of a clinical trial success rating or a drug or genetic association score for the biological entity pair.

23. The computer-implemented method of claim 1, wherein the biological entity pair comprises a disease-target pair and the target comprises a gene, a nucleic acid or a protein associated with the disease that may be targeted by a compound, a ligand, a drug, or a cell therapy.

24. The computer-implemented method of processing a database of claim 12, the method further comprising:

automatically deleting the identified biological entity pairs from the database or flagging the identified biological entity pairs for deletion; and/or labelling the identified biological entity pairs as being excluded from any downstream analysis of data in the database.

* * * * *